US006545046B2

(12) United States Patent
Sherratt et al.

(10) Patent No.: US 6,545,046 B2
(45) Date of Patent: Apr. 8, 2003

(54) METHOD FOR ENHANCED DELIVERY OF OXYBUTYNIN AND COMPOSITIONS THEREOF

(75) Inventors: Amanda J. Sherratt, Lexington, KY (US); Abdulghan A. Houdi, Lexington, KY (US)

(73) Assignee: Theramax Inc.

( * ) Notice: Subject to any disclaimer, the term of this patent is extended or adjusted under 35 U.S.C. 154(b) by 0 days.

(21) Appl. No.: 09/792,581

(22) Filed: Feb. 23, 2001

(65) Prior Publication Data
US 2002/0161044 A1 Oct. 31, 2002

Related U.S. Application Data
(60) Provisional application No. 60/229,107, filed on Aug. 30, 2000.

(51) Int. Cl.$^7$ .............................................. A61K 31/24
(52) U.S. Cl. ...................................................... 514/534
(58) Field of Search .......................................... 514/534

(56) References Cited

U.S. PATENT DOCUMENTS

| 5,500,222 A | 3/1996 | Lee et al. ..................... 424/448 |
| 5,674,895 A | 10/1997 | Guittard et al. .............. 514/534 |
| 5,736,577 A | 4/1998 | Aberg et al. ................. 514/617 |
| 5,840,754 A | 11/1998 | Guittard et al. .............. 514/534 |
| 6,039,967 A | 3/2000 | Ottoboni et al. ............. 424/426 |

OTHER PUBLICATIONS

MEDLINE 20479916, Kao et al, Pharm. Res., abstract, Aug. 2000, 17 (8), 978–84.*
CA130:218113, Buyse et al, J. Urol., abstract, 1998, 160 (3, Pt. 1), 892–896.*
MEDLINE 97038955, Cicinelli et al, J. Endocrin. Investig., abstract, Jul.–Aug. 1996, 19 (7), 427–32.*
Hirai, et al., "Nasal absorption of insulin in dogs" Diabetes 27:296–299 (1978).
Genitourin Smooth Muscle Relaxants; AHFS Drug Information 86:12 3164–3165 (1999).
Physician Desk Reference "Ditropan" Edition 54 507–508 (2000).
Bonney, et al. "Topical Effect of Intravesical Oxybutynin" J. Urology vol. 150 1522–1525 (1993).
Fisher et al., "The effect of molecular size on the nasal absorption of water–soluble compounds in the albino rat" J. Pharm Pharmacol. 39:357–362, 1986.
Hussain, et al., "Nasal Absorption of Propanolol in Rats" J. Pharm Sci. vol. 68, No. 9, (1979).
Hussain, et al., "Nasal Absorption of Propanolol in Humans" J. Pharm Sci. vol. 69, No. 10, (1980).
Aaltonen, et al. "Antimuscarinic Activity of Oxybutynin in the Human Plasma Quantitated by a Radioreceptor Assay" Acta Pharm. 55, 100–103 (1984).

Bawarsh–Nassar, et al. "Nasal absorption of 17 α–ethinyloestradiol in Rat" J. Pharm. 41:214–215 (1989).
Buyse. et al. "Intravesical Oxybutynin for Neurogenic Bladder Dysfunction: Less Systemic Side Effects Due to Reduced First Pass Metabolism" J. Urology vol. 160, 892–896 (1998).
Connor, et al. "Early Cystometrograms can Predict the Response to Intravesical Instillation of Oxybutynin Chloride in Myelomeningocele Patients" J. Urology vol. 151, 1045–1047 (1994).
Douchamps, et al. "The Pharmacokinetics of Oxybutynin in Man" Eur. J. Clin. Pharm. 35: 515–520 (1988).
Eriksen, et al. The systemic availability if buprenorphine administered by nasal spray: J. Pharm 41: 803–805 (1989).
Hernandez, et al. "Nonsurgical management of threatened upper urinary tracts and incontinence in children with myelomeningocele" J. Urology vol. 152 1582–1585 (1994).
Kasabian, et al. "The use of intravesical oxybutynin chloride in patients with detrusor hypertonicity and detrusor hyoerreflexia" J. Urology vol. 151 944–945 (1994).
Madersbacher, et al. "Control of Detrusor Hyperreflexia by the Intravesical Instillation of Oxybutynine Hydrochloride" Paraplegia vol. 29 84–90 (1991).
Hughes, et al. "Measurement of Oxybutynin and its η–desethyl Metabolite in Plasma, and its application to Pharmacokinetic studies in young, elderly and frail elderly volunteers" Xenobiotica vol. 22, No. 7, 859–869 (1992).
Madersbacher, et al. "Intravesical Application of Oxybutynin: Mode of Action in Controlling Detrusor Hyperreflexia" Eur Urol. 28: 340–344 (1995).
Massad, et al. "The Pharmacokinetics of Intravesical and Oral Oxybutynin Chloride" J. Urology vol. 148 595–597 (1992).
Palmer, et al. "Complications of Intravesical Oxybutynin Chloride Therapy in the Pediatric Myelomeningocele Population" J. Urology vol. 157 638–640 (1997).
Postlind, et al. "Tolterodine, A new Muscarinic Receptor Antagonist, is Metabolized by Cytochromes P450 2D6 and 3A in Human Liver Microsomes" Drug Metabolism & Disposition vol. 26, No. 4 289–293 (1998).
Waldeck, et al. "Comparison of Oxybutynin and its Active Metabolite, N–Desethyl–Oxybutyniin, in the Human Detresor and Parotid Gland" J. Urology vol. 157, 1093–1097 (1997).

(List continued on next page.)

Primary Examiner—Rebecca Cook
(74) Attorney, Agent, or Firm—Davidson, Davidson & Kappel, LLC

(57) ABSTRACT

This invention provides to a method for enhancement of systemic delivery of oxybutynin by administration via the nasal route, and methods of treatment comprising intranasal administration of oxybutynin. The present invention further provides pharmaceutical compositions comprising oxybutynin and/or pharmaceutically acceptable salts thereof.

20 Claims, 2 Drawing Sheets

OTHER PUBLICATIONS

Lindeke, et al. "Metabolism of Oxybutynin: Establishment of Desethyloxybutynin and Oxybutynin η–Oxide Formation in Rat Liver Preparations Using Deuterium Substitution and Gas Chromatographic Mass Spectrometric Analysis" Biomedical Mass Spectrometry, vol. 8, No. 10 506–513 (1981).

Kao, et al. "Enhancement of the Systemic and CNS Specific Delivery of L–Dopa by the Nasal Administration of its Water Soluble Prodrugs" Pharm Res. vol. 17 No. 8 978–984 (2000).

Hodge, et al. "Immunoglobulin A (IgA) Responses and IgE–Associated Inflammation along the Respiratory Tract after Mucosal but Not Systemic Immunization" Infection & Immunity vol. 69 No. 4 2328–2338 (2001).

Ayres, et al, "Absorption, pharmacokinetics and metabolism of $^{14}$C–sumatriptan following intranasal administration to the rat" Xenobiotica, vol. 26, No. 12, 1273–1282, (1996).

Bergstrom, et al, "Deposition and Disposition of [$^{11}$C] Zanamivir Following Administration as an Intranasal Spray" Clin Pharmacokinet, 33–39 (1999).

Sakane, et al, "Transport of Cephalexin to the cerebrospinal fluid directly from the nasal cavity" J. Pharm. Pharmacol 43: 449–451 (1991).

* cited by examiner

Oxybutynin

N-desethyloxybutynin

METHOD FOR ENHANCED DELIVERY OF OXYBUTYNIN AND COMPOSITIONS THEREOF

This application claims the benefit of U.S. provisional application No. 60/229,107 filed Aug. 30, 2000, the disclosure of which is hereby incorporated by reference.

BACKGROUND OF THE INVENTION

1. Field of the Invention

This invention relates to compositions for enhancement of delivery of oxubutynin, antimuscarinic and spasmolytic drugs, by administration via the nasal route to treat patients suffering from overactive bladder with symptoms of urinary urgency, frequency or urge incontinence. The invention is also directed to methods of treatment thereof, and methods of preparation thereof.

2. Description of the Related Art

U.S. Pat. No. 6,039,967 to Ottoboni, describes an intravesical drug delivery system for placement of oxybutynin into the bladder through the urethra.

U.S. Pat. No. 5,840,754 to Guittar, describes the administration of a controlled-release dosage form tablet comprising oxybutynin to lessen the incidence of side effects.

U.S. Pat. No. 5,736,577 to Aberg, describes the use of optically pure (S)-oxybutynin for treating urinary incontinence.

U.S. Pat. No. 5,674,895 to Guittard, describes a rate-controlled tablet dosage form of oxybutynin.

U.S. Pat. No. 5,500,222 to Lee, describes the transdermal administration of oxybutynin together with a suitable permeation enhancer.

Oxybutynin, [Benzeneacetic acid, a-cyclohexyl-a-hydroxy-4-(diethylamino)-2-butynyl ester], a tertiary amine with antimuscarinic, spasmolytic and local anesthetic properties, is currently used for the treatment of overactive bladder with symptoms of urinary urgency, frequency or urge incontinence due to detrusor instability or detrusor hyperreflexia. Oxybutynin is currently marketed in the United States under the trade names Ditropan and Ditropan XL as an oral dosage form (*Physician's Desk Reference*, pp 507, 54$^{th}$ Edition, 2000).

After oral administration of oxybutynin, low systemic bioavailability (<6%) is observed because of extensive first-pass metabolism (Douchamps et al., *Eur. J. Clin. Pharmacol.* 35:515, 1988). Oxybutynin is metabolized in the liver and it has been suggested that the metabolite N-desethyloxybutynin, is pharmacologically active (Lindeke et al., *Biomed. Mass. Spec.* 8: 506, 1981; Aaitonen et al., *Acta Pharmacol. Toxicol.* 55: 100, 1984) and is associated with the systemic side effects following oral treatment with oxybutynin (Buyse et al., *J. Urology* 160:892, 1998). Measurements of oxybutynin and N-desethyloxybutynin plasma levels after oral administration of oxybutynin resulted in a considerably larger (5 to 11 fold) concentration of the metabolite compared with the parent compound (Hughes et al, *Xenobiotica* 22: 859, 1992). Functional and receptor binding experiments have also demonstrated that N-desethyloxybutynin has similar anticholinergic activity to the parent compound on isolated human bladder and parotid gland (Waldeck et al.,*J. Urology* 157: 1093, 1997). Despite the clinical success of intravesical oxybutynin, the exact mechanism of action remains unknown. As systemic side effects were generally absent when the drug was applied intravesically (Buyse et al., *J. Urology* 160:892, 1998), it has been suggested that oxybutynin was not absorbed into the blood stream and that its efficacy resulted from a profound local effect alone. Measurements of plasma levels of oxybutynin after intravesical and oral administration revealed extensive inter-individual variations, but clearly there was substantial absorption of the drug after intravesical application and therefore its effect on detrusor muscle was believed to be mainly systemic due to its absorption (Madersbacher and Jilg, *Paraplegia* 29: 84, 1991; Massad et al., *J. Urology* 148: 595, 1992; Madersbacher and Knoll, *Eur. J. Urology* 28: 340, 1995). Although no measurements of circulating metabolites were performed in these studies, it has been speculated that a difference in metabolite concentration, due to reduced first pass metabolism, could explain the difference in systemic side effects. Alternatively, there might be a different metabolism after oral administration, compared with intravesical instillation, due to enzymatic reactions in the alimentary tract. In contrast to the promising clinical results of intravesical oxybutynin therapy, patient withdrawal was significant (up to 65%) in several studies, mainly due to practical inconvenience and, to a lesser extent, untoward effects (Kasabian et al., *J. Urol.* 151: 944, 1994; Connor et al., *J. Urol.* 151: 1045, 1994; Palmer et al., *J. Urol.* 157:638, 1997). Hernandez et al. concluded that the only disadvantage to intravesical therapy appeared to be variable long-term patient compliance (Hernandez et al., *J. Urol.* 152:1582, 1994).

Among the adverse effects of oxybutynin following oral administration include dry mouth, constipation, diarrhea, nausea, vomiting, somnolence, dizziness, headache pain, insomnia, tachycardia (*Physician's Desk Reference*, pp 507, 54$^{th}$ Edition, 2000; *Drug Information, AHFS* 99: pp. 3164, 1999). In clinical studies, adverse reactions requiring discontinuance of oxybutynin therapy (5 mg 3 times daily) occurred in about 20% of patients.

Therefore, in view of the aforementioned deficiencies attendant with prior art compositions and methods of oxybutynin administration, it should be apparent that there still exists a need in the art for a safe and convenient composition and method for administering oxybutynin to patients at safe and effective doses. To the best of applicants' knowledge, nasal administration of oxybutynin is unknown and completely unsuggested by the art.

While nasal administration has become an accepted route of administration, the following disclosures limit that mode of delivery to specific drugs described. Moreover, it has been observed that many therapeutic agents cannot be usefully administered by this unusual route. Consequently, nasal administration remains a technique for which applicability is far from universal and the results unpredictable.

SUMMARY OF THE INVENTION

Accordingly, a major object of the present invention is to provide a composition and method for the safe, convenient and effective way of administering the useful drugs oxybutynin to a patient in need of such treatment. The method comprises intranasal administration of an effective amount of oxybutynin for the treatment of overactive bladder with symptoms of urinary urgency, frequency or urge incontinence and other disorders.

Nasal drug administration serves as an alternative route of drug administration. It has been shown that most drugs administered nasally produce plasma levels similar to those following intravenous administration (Hussain, et al., *J. Pharm. Sci.* 69:1240, 1980; Bawarshi-Nassar et al., *J.*

Pharm. Pharmacol 41: 214, 1989; Hussa in, et al., J. Pharm. Sci. 68: 1196, 1979). The nasal delivery route is a very useful method of drug administration, which frequently improves drug bioavailability by direct absorption into the circulation avoiding hepatic first-pass metabolism and destruction in the gastrointestinal tract following oral delivery of drug (Chien, et al., Marcel Dekker, New York, 1989.).

The objective of the present inventions is to improve oxybutynin bioavailability by administering oxybutynin via the nasal route in order to reduce the dose required for its beneficial effect. Intranasal oxybutynin delivery will improve drug bioavailability by direct absorption into the circulation avoiding extensive hepatic first-pass metabolism which significantly lowers the plasma concentrations of oxybutynin administered orally. Therefore, small doses of oxybutynin can be administered which will results in fewer side effects, and the drug will be more tolerable and more effective in treating patients suffering from overactive bladder with symptoms of urinary urgency, frequency or urge incontinence and other disorders described above. Additionally, as oxybutynin is heavily metabolized by the liver, administration by the nasal route will help to reduce drug—drug interactions with other drugs that are also extensively metabolized by the liver.

Nasal administration of oxybutynin would be expected by the Applicants to increase oxybutynin blood levels with a concomitant decrease in blood levels of their major metabolites N-desethyloxybutynin. This expected increase by Applicant in drug concentration ratio of unchanged oxybutynin to metabolite in the systemic circulation is even more significant in light of studies which indicate the association of the major metabolites N-desethyloxybutynin with significant side effects.

In addition, nasal oxybutynin administration is easy and convenient. Furthermore, in many situations it has already been shown that the onset and extent of drug delivery after intranasal administration is comparable to the same drug and dose being given intravenously. Therefore, intranasal delivery of drug for treatment of overactive bladder with symptoms of urinary urgency such as oxybutynin could be used in those situations where a rapid or intermittent drug effect is desired.

In certain embodiments, the invention is directed to a method of providing oxybutynin therapy to a patient in need thereof comprising intranasally administering an effective amount of oxybutynin or a pharmaceutically acceptable salt thereof to said patient and compositions thereof. Preferably, the oxubutynin is administered with a pharmaceutically acceptable carrier which can be in the form of, e.g. a solution, suspension, gel, ointment, lotion, semi-solid, vaporizable carrier, a powder and combination thereof. In certain embodiments, the carrier can provide a sustained release of the drug.

In certain embodiments, the invention is directed to a method of reducing side effects associated with oxybutynin therapy comprising administering a therapeutically effective amount of oxybutynin intranasally, the intranasal administration reducing side effects associated with the oral administration of an equivalent dose of oxybutynin. In certain embodiments, the intranasal administration reduces side effects by reducing the formation of the N-desethyl metabolite of oxybutynin as compared to an equivalent dose of oral oxybutynin.

In certain embodiments, the ratio of the plasma concentration of the desmethyl metabolite of oxybutynin after said intranasal administration to the plasma concentration of the N-desethyl metabolite of oxybutynin after the oral administration is less than about 1:5, less than about 1:10 or less than about 1:20.

In certain embodiments, the ratio of the plasma concentration of the N-desethyl metabolite said nasal administration to the plasma concentration of oxybutynin is less than about 2:1, less than about 1:1, less than about 0.75:1, or less than about 0.55:1.

In certain embodiments, the bioavailability of the of the intranasal oxybutynin is increased as compared to an equivalent dose of oral oxybutynin. In preferred embodiments, the ratio of the AUC after intranasal oxybutynin to AUC of oxybutynin after an equivalent dose of oral oxybutynin is at least 2:1 or at least 4:1, and preferably at least 8:1 or at least 10:1. In certain embodiments, the ratio is based on the absolute AUC and other embodiments the AUC is measured at 2 hours after administration. The ratios are also based on the oral oxybutynin being administered as a solution or a tablet.

With the foregoing and other objects, advantages and features of the invention that will become hereinafter apparent, the nature of the invention is further explained in the following detailed description of the preferred embodiments of the invention and in the appended claims.

DETAILED DESCRIPTION OF THE PREFERRED EMBODIMENTS OF THE INVENTION

Figure 1:
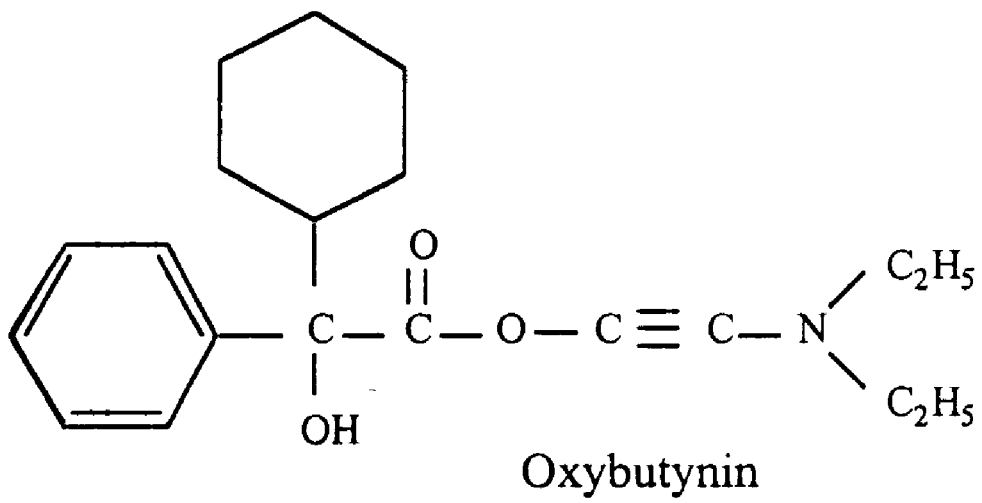
FIG. 1. depicts the structures of oxybutynin and its major metabolite N-desethyloxybutynin.
Figure 1:
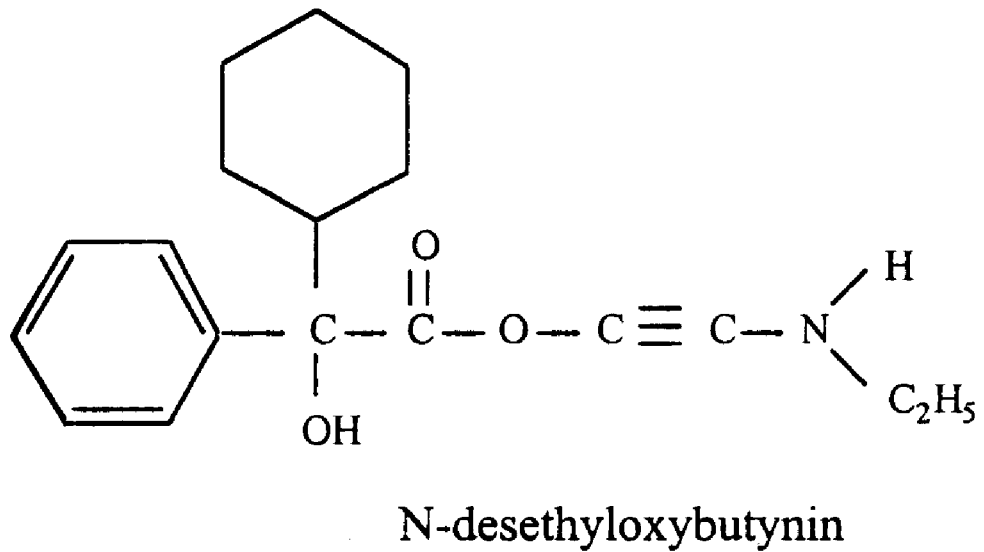

Orally administered oxybutynin currently available on the market show extensive first pass metabolism with a ten-fold variation between subjects. Thus, the present inventions have discovered a novel composition and method for the delivery of oxybutynin to a patient in need of such treatment, comprising the intranasal administration of oxybutynin. This composition and method offers significant clinical advantages over the prior art. More specifically, the inventors sought to provide a safe, effective, fast and convenient treatment for administering oxybutynin to a patient in need of such treatment, which comprises the administration of oxybutynin intranasally, thus avoiding the side-effects and other disadvantages associated with oral dosage forms. Specifically, smaller doses of oxybutynin can be administered through the nasal route, thus resulting in rapid onset of action, fewer side effects and reducing drug—drug interactions. By using the composition and method of the present invention, the drug will become more tolerable and more effective in treating patients suffering from overactive bladder with symptoms of urinary urgency, frequency or urge incontinence.

Intranasal administration of oxybutynin is as effective as oral administration, but may be conveniently and painlessly self-administered by the patient, and at lower doses and faster onset of action compared to oral dosage forms, thereby allowing a decreased incidence of side effects and decreased incidence of drug—drug interactions and faster onset of action compared to the oral administration.

As used in the present invention, the term "oxybutynin" will be understood to refer to either (R)-oxybutynin, (S)-oxybutynin, or a racemic mixture of (R)- and (S)-oxybutynin.

According to the present invention, oxybutynin and other related compounds and their metabolites may be administered either as a free base, or in the form of a pharmaceutically acceptable salt thereof. Pharmaceutically acceptable salts of an acid group or an amino group include, but are not limited to, salts of both inorganic or organic acids, for example: acetic, fumaric, benzoic, ascorbic, pamoic, lactic, tartaric, maleic, isothionic, lactobionic, succinic, oxalic, propionic, citric, gluconic, aspartic, stearic, palmitic itaconic, glycolic, p-aminobenzoic, glutamic, salicylic, bismethylenesalicylic, methanesulfonic, ethandisulfonic, ethanesulfonic, benzenesulfonic, cyclohexylsulfamic, p-tolylsulfonic, hydrobromic, hydrochloric, sulfuric, phosphoric, nitric, and sulfamic acids. In a particularly preferred embodiment, the pharmaceutically acceptable salt is oxybutynin chloride because of good water solubility.

A still further aspect of this invention is a pharmaceutical composition of matter that comprises oxybutynin as described above, and/or pharmaceutically acceptable salts thereof, and at least one pharmaceutically acceptable carrier suitable for nasal administration.

For therapeutic use for overactive bladder with symptoms of urinary urgency, frequency or urge incontinence and other disorders described above, oxybutynin, or its salt can be conveniently administered in the form of a pharmaceutical composition containing oxybutynin, its salt, and a pharmaceutically acceptable carrier thereof. Suitable carriers are well known to those skilled in the art and vary with the desired form and mode of administration of the pharmaceutical composition. Typically, the carrier may be a liquid, solution, suspension, gel, ointment, lotion, semi-solid, or vaporizable carrier, or combinations thereof. In a preferred embodiment, the carrier is a pharmaceutically acceptable aqueous carrier. Such compositions are prepared in accordance with accepted pharmaceutical procedures, for example, as described in Remington's Pharmaceutical Sciences, seventeen edition, ed. Alfonso R. Gennaro, Mack Publishing Company, Easton, Pa., Eighteenth edition (1990), which is hereby incorporated by reference. The drug can also be in powder form without the need for further excipient.

The compound of the invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. To prepare formulations suitable for intranasal administration, solutions and suspensions are sterilized and are preferably isotonic to blood.

The formulations may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art (see Remington's Pharmaceutical Sciences, seventeenth edition, ed. Alfonso R. Gennaro, Mack Publishing Company, Easton, Pa., Eighteenth edition, 1990). For example, the oxybutynin can be administered into the nasal passages by means of a simple dropper a dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

In addition to the ingredients particularly mentioned above, the formulations of this invention may also include other agents conventional in the art for this type of pharmaceutical formulation. For example, the nasal formulation can provide a sustained release of the drug in order for e.g., once or twice daily. Suitable sustained release materials include cellulosic derivatives which adheres to the nasal mucosa, as described in EP 205282, hereby incorporated by reference.

The present invention is also directed to a method of treating overactive bladder with symptoms of urinary urgency, frequency or urge incontinence, and to a method for treating other disorders in a patient by treating that patient with an effective amount of oxybutynin intranasally. According to the present invention, the term "patient" will encompass any mammal requiring treatment with oxybutynin, particularly a human patient suffering from overactive bladder with symptoms of urinary urgency, frequency or urge incontinence, or human patient suffering from other disorders requiring such treatment.

The dosage of oxybutynin or pharmaceutically acceptable salts thereof in the compositions of the invention will vary depending on several factors, including, but not limited to, age, weight, and species of patient, the general health of the patient, the severity of the symptoms, whether the composition is being administered alone or in combination with other agents, the incidence of side effects and the like. The desired dose may be administered as 1 to 6 or more subdoses administered at appropriate intervals throughout the day. The compounds may be administered repeatedly over a period of months or years. Higher and lower doses may also be administered. For example, a dose of oxybutynin can be from 0.01 mg per dose to 50 mg per dose, e.g., 0.5 mg, 1 mg, 1.5 mg, 2 mg, 2.5 mg, 3 mg 5 mg, 7.5 mg 10 mg or 15 mg.

The daily dose may be adjusted taking into account, for example, the above-identified variety of parameters. Typically, oxybutynin or its derivatives may be administered in an amount of up to about 50 mg/day. However, other amounts may also be administered depends on the relative potency of the basic compound, the specific biological activity and the conditions of the patient.

To achieve good plasma concentrations, the oxybutynin may be administered, for instance, by intranasal administration of an approximate 0.1 to 1M solution of the active ingredient, optionally in saline.

While it is possible for the active ingredient to be administered alone, it is preferably present as a pharmaceutical formulation. The formulations of the present invention comprise of at least one active ingredient, as defined above, together with one or more acceptable thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents, e.g., other anticholinergic or any other agents used for disorders described above. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

In vivo Nasal Delivery of Oxybutynin

Surgical Procedures:

The nasal absorption of oxybutynin was studied using an in vivo technique described previously (1). Male Sprague-Dawley rats (body weight 250±25 gm) were used in these studies. Animals were fasted overnight prior to experimentation. Surgical procedures were performed under equithesin anesthesia (3 ml/kg, i.p.). An incision was made in the neck, and the trachea cannulated with polyethylene tubing (PE-260). A closed end tube was inserted through the esophagus to the posterior part of the nasal cavity to prevent drug from entering the esophagus. The nasopalatine passage was then closed with an adhesive agent to prevent drainage of the drug from the nasal cavity to the mouth.

Blood samples were collected from a cannula inserted into the femoral artery. For intravenous drug administration, the jugular vein was cannulated.

Experimental Procedure:

Solutions of oxybutynin hydrochloride (5 mg/kg/100 µl) were prepared in normal saline and administered through the right nostril using a microsyringe. For oral administration, rats received an aqueous solution of oxybutynin hydrochloride (5 mg/kg) administered by gavage tube. For intravenous (i.v.) administration, the same dose of oxybutynin was injected into the jugular vein (1 ml/kg body weight). Blood samples after oxybutynin administration were collected before and at 0, 5, 10, 20, 40 and 60 min after drug administration, centrifuged, and serum removed and stored (−70° C.) until analysis.

Differences in the plasma oxybutynin or N-desethyloxybutynin concentrations between i.v., oral, and nasal delivery routes were compared using the Student's t test.

Extraction and HPLC Analysis of Oxybutynin and its Metabolite:

Analysis of oxybutynin and its metabolites N-desethyloxybutynin were performed using HPLC as described by Buyse et al. (2). Extraction of standards for calibration curve and plasma samples were performed as described previously by Hughes et al. (3).

Oxybutynin and its metabolite (N-desethyloxybutynin) were analyzed using a reverse-phase column (25 cm×46 mm I.D.) and eluted with mobile phase consisting of 50% acetonitrile in 10 nmol/L potassium phosphate buffer, pH 6.3. The mixture was filtered and degassed prior to use. The flow rate was 0.7 ml/min, and the effluent was monitored with a dual UV detector system at 210 nm.

All determinations were performed by calculating the area ratios of each compound to the internal standard. Unknown amounts were determined from calibration curves run with each day's unknown analysis.

Results and Discussion

Figure 2:
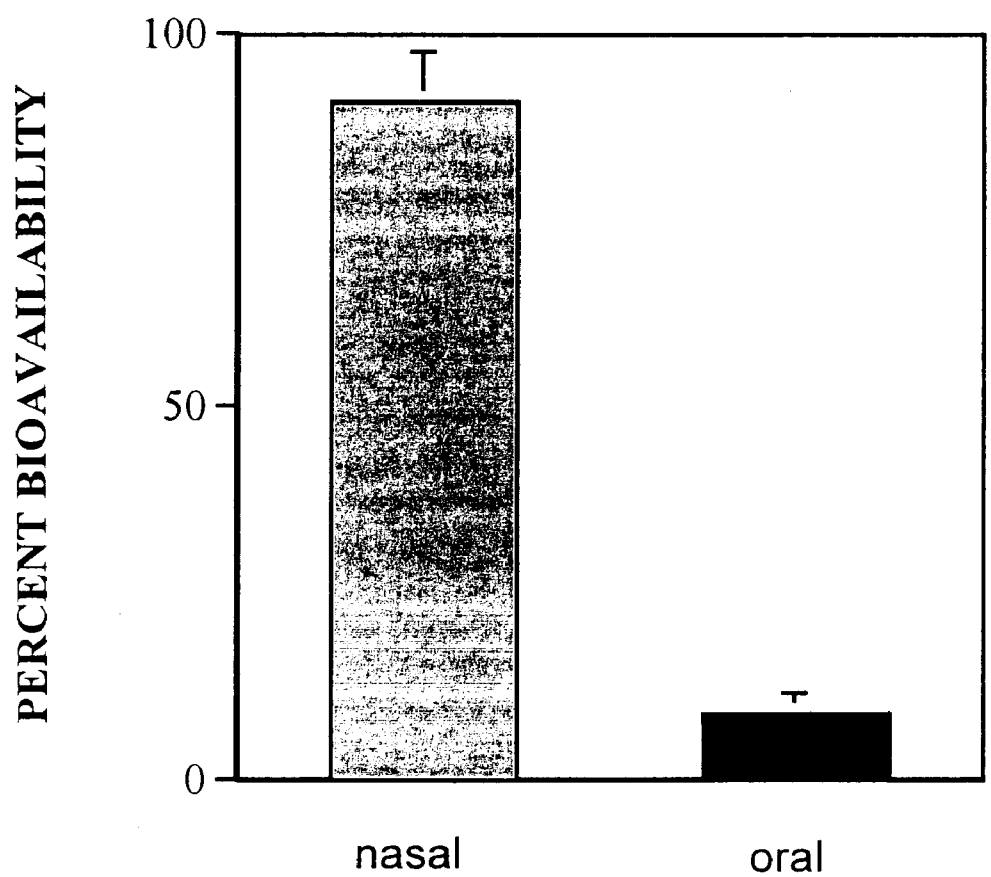
FIG. 2 is a bar graph of oxybutynin (5 mg/kg) bioavailability in rats following nasal and oral administration, relative to the intravenous administration (100%). Data presented as mean ±SEM (n=4).

Our data shows a large improvement (~10 fold increase) in the bioavailability of oxybutynin after intranasal administration compared to orally administered oxybutynin. Bioavailability of orally administered oxybutynin was very low, approximately 9%, due to extensive first pass metabolism (FIG. 2). The high bioavailability of intranasal oxybutynin (90%) indicates circumvention of the first-pass effect. This improvement in oxybutynin bioavailability means significantly less amount of oxybutynin will be needed for intended treatment. In addition to improvement in bioavailability, the rapid absorption of the intranasally administered oxybutynin allows the drug into the systemic circulation almost instantly ($t_{max}$=10 min, Table 1). The $t_{max}$ of orally administered oxybutynin was approximately 30–40 min. The orally administered oxybutynin in our experiment was delivered as a solution of oxybutynin in water. We will expect the $t_{max}$ of orally administered oxybutynin as a solid dosage form (tablet) currently available in the market will take longer than 40 min. This is another significant advantage of nasally administered oxybutynin.

The high bioavailability of intranasal oxybutynin is dependent upon the relative rates of intranasal absorption versus elimination of the formulated dose from the nasal cavities by mucociliary clearance and drainage. Both absorption and drainage can be affected by the unique physiochemical characters of the compound under investigation and the formulation used (4, 5). Our data prove that the physiochemical properties of oxybutynin makes it an excellent candidate drug for nasal delivery which presents a novel and unobvious drug characteristic.

TABLE 1

Concentration ratio of oxybutynin and its metabolite, N-desethyloxybutynin in rat over 1 hr following an oral or intranasal dose of oxybutynin (5 mg/kg). Data expressed as mean ± SEM. Results generated from 4 rats per group.

| | Oxybutynin | N-desethyloxybutynin | Ratio N-desethyloxybutynin/ Oxybutynin |
|---|---|---|---|
| Oral | | | 12.39 ± 2.1 |
| $t_{max}$ | 40 min | 1.1 h | |
| $AUC_{0-2 h}$ | 180 ± 53 | 2230 ± 479 | |
| Nasal | | | 0.55 ± 0.137 |
| $t_{max}$ | 10 min | 1.6 h | |
| $AUC_{0-2 h}$ | 1770 ± 190 | 970 ± 179 | |

Since one of the major metabolites of oxybutynin, N-desethyloxybutynin is associated with adverse effects (dry mouth, nausea, constipation . . . etc.) which leads to decrease patient compliance with the treatment (2), we also measured the concentration of this metabolite, (N-desethyloxybutynin), in plasma following oral or nasal administration of oxybutynin (5 mg/kg) and to investigate whether the level of this metabolite could be reduced by nasal delivery of the drug. The relative plasma levels of oxybutynin and N-desethyloxybutynin are shown in Table 1. The data in Table 1 are presented as a ratio of the oxybutynin major metabolite, N-desethyloxybutynin, to parent compound oxybutynin, to emphasize the benefit of comparing nasal vs oral routes of administration in reducing metabolite levels (high metabolite levels associated with poor clinical outcome). Following oral administration of oxybutynin to rats, the concentration of N-desethyloxybutynin was approximately 12 fold greater than that of the parent compound oxybutynin in plasma. Following nasal administration of oxybutynin to rats, the plasma concentration of N-desethyloxybutynin was around half (0.55) of that of oxybutynin. This is a new finding and a particularly important factor in developing appropriate dosage forms for human use in which less of the oxybutynin will be transformed to N-desethyloxybutynin. It has been reported in human that higher plasma metabolite concentrations N-desethyloxybutynin is associated with adverse effects and decreased patient compliance with the treatment (2). Therefore nasal delivery of oxybutynin will avoid first pass metabolism of oxybutynin and will allow the drug to be distributed to the site of action prior to metabolism to N-desethyloxybutynin. Indeed our data with the nasal delivery of oxybutynin showed a significant reduction in the level of N-desethyloxybutynin. Our findings with the nasal delivery of oxybutynin will be have important impact when applied to humans.

In conclusion, the present data demonstrates that improved bioavailability and reduced first-pass metabolism of intranasal oxybutynin results in a significantly lower concentration ratio of N-desethyloxybutynin over the parent compound oxybutynin than is observed following oral administration, that will explain the clinically relevant reduction of side effects that characterize intranasal treatment. Furthermore, the rapid absorption of oxybutynin through the nasal cavity provides rapid onset of action of the drug, an almost instant therapeutic effect which is a major advantage over the oral delivery system. In addition nasal delivery of oxybutynin will improve and reduce the inter-individual variability that has been reported previously after oral intake; genetic polymorphism, with some patients being poor metabolizers, has been suggested to explain the variation.

EXAMPLE 2

Nasal Spray Solution

| Oxybutynin chloride | 250 mg |
|---|---|
| Isotonic Saline | q.s. |
| | 10 ml |

Oxybutynin is dissolved in sterile isotonic saline and the pH adjusted to 7.4. The solution is placed in a nasal administrator designed to deliver 0.1 ml of spray for each application. One spray in each nostril will deliver a total of 5 mg of oxybutynin.

EXAMPLE 3

Nasal Gel (Aqueous)

| Oxybutynin | 250 mg |
|---|---|
| Methocel | 3 gm |
| Water | 100 gm |

Approximately 7 gm of water is heated to 80° C., and the methocel is dispersed in it with stirring. The oxybutynin is dissolved in 30 gm of water at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

EXAMPLE 4

Nasal Spray Solution

| Oxybutynin chloride | 50 mg |
|---|---|
| Isotonic Saline | 10 ml |

Oxybutynin is dissolved in sterile isotonic saline and the pH adjusted to 7.4. The solution is placed in a nasal administrator designed to deliver 0.1 ml of spray for each application. One spray in each nostril will deliver a total of 1 mg of oxybutynin.

EXAMPLE 5

Nasal Gel (Aqueous)

| Oxybutynin | 50 mg |
|---|---|
| Methocel | 3 gm |
| Water | 100 gm |

Approximately 7 gm of water is heated to 80° C., and the methocel is dispersed in it with stirring. The oxybutynin is dissolved in 30 gm of water at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

What is claimed is:

1. A method of providing oxybutynin therapy to a patient in need thereof comprising intranasally administering an effective amount of oxybutynin or a pharmaceutically acceptable salt thereof to said patient.

2. The method of claim 1 wherein said oxubutynin is administered with a pharmaceutically acceptable carrier.

3. The method of claim 2 wherein the carrier is selected from the group consisting of a solution, suspension, gel, ointment, lotion, semi-solid, vaporizable carrier, and powder or a combination thereof.

4. The method of claim 1 wherein said oxybutynin is selected from the group consisting of oxybutynin base, R-oxybutynin base, and S-oxybutynin base or a pharmaceutically acceptable salt thereof or a and mixture thereof.

5. A pharmaceutical composition for nasal administration comprising oxybutynin, a pharmaceutically acceptable salt thereof, or a mixture thereof; and a pharmaceutically acceptable carrier suitable for nasal administration selected from the group consisting of a normal saline solution, a suspension, a gel, an ointment, a lotion, a semi-solid, a vaporizable carrier and a powder or a combination thereof.

6. The composition of claim 5 wherein the carrier provides a sustained release of the oxybutynin.

7. A method of reducing side effects associated with oxybutynin therapy comprising administering a therapeutically effective amount of oxybutynin intranasally, said intranasal administration reducing side effects associated with the oral administration of an equivalent dose of oxybutynin.

8. The method of claim 7 wherein said intranasal administration reduces side effects by reducing the formation of the N-desethyl metabolite of oxybutynin as compared to an equivalent dose of oral oxybutynin.

9. The method of claim 8 wherein the ratio of the plasma concentration of the desmethyl metabolite of oxybutynin after said intranasal administration to the plasma concentration of the N-desethyl metabolite of oxybutynin after said oral administration is less than about 1:5.

10. The method of claim 9 wherein said ratio is less than about 1:10.

11. The method of claim 9 wherein said ratio is less than about 1:20.

12. The method of claim 7 wherein the ratio of the plasma concentration of the N-desethyl metabolite said nasal administration to the plasma concentration of oxybutynin is less than about 2:1.

13. The method of claim 12 wherein the ratio is less than about 1:1.

14. The method of claim 12 wherein the ratio is less than about 0.75:1.

15. The method of claim 12 wherein the ratio is less than about 0.55:1.

16. A method of increasing the bioavailability of oxybutynin comprising administering intranasally the composition of claim 5 whereby the bioavailability of the intranasal oxybutynin is increased as compared to an equivalent dose of oral oxybutynin.

17. The method of claim 16 wherein the ratio of the AUC of oxybutynin after intranasal oxybutynin to AUC of oxybutynin after an equivalent dose of oral oxybutynin is at least 2:1.

18. The method of claim 17 wherein said ratio is at least 4:1.

19. The method of claim 17 wherein said ratio is at least 8:1.

20. The method of claim 17 wherein said ratio is at least 10:1.

* * * * *